US005641624A

United States Patent [19]
Povolotsky et al.

[11] Patent Number: 5,641,624
[45] Date of Patent: Jun. 24, 1997

[54] METHOD FOR MEASURING ANTI-HIV-1 P24 ANTIBODY AND USE THEREOF

[75] Inventors: Jacob L. Povolotsky, Brooklyn; Bruce W. Polsky; Donald Armstrong, both of New York, all of N.Y.

[73] Assignee: Sloan-Kettering Institute for Cancer Research, New York, N.Y.

[21] Appl. No.: 253,114

[22] Filed: Jun. 2, 1994

[51] Int. Cl.⁶ .................................................. C12Q 1/70
[52] U.S. Cl. .............................. 435/5; 435/7.1; 435/7.9; 435/7.92; 435/7.93; 435/7.95; 435/961; 435/974; 435/975; 436/518; 436/528; 436/531
[58] Field of Search ...................... 435/5, 7.1, 7.72, 435/7.9, 7.92, 7.93, 7.95, 961, 974, 975; 436/518, 528, 531

[56] References Cited

U.S. PATENT DOCUMENTS

| 4,604,348 | 8/1986 | Neurath ................................ 435/7 |
| 4,870,003 | 9/1989 | Kortright et al. ..................... 435/5 |
| 5,183,740 | 2/1993 | Ligler et al. ...................... 435/7.32 |
| 5,206,177 | 4/1993 | DeLaCroix et al. ............... 436/518 |
| 5,340,748 | 8/1994 | Baugher et al. .................. 436/518 |
| 5,354,654 | 10/1994 | Ligler et al. ........................ 435/5 |

OTHER PUBLICATIONS

Allain, J. -P., et al. (1986) Serological Markers in Early Stages of Human Immunodeficiency Virus Infection in Haemophiliacs, *The Lancet* II:1233–1236 (Exhibit 2).

Andrieu, J. -M. et al. (1988) Serum HIV Antigen and Anti–p24–Antibodies in 200 HIV Seropositive Patients: Correlation with CD24 and CD8 Lymphocyte Subsets, *Clin. Exp. Immuno.* 73:1–5 (Exhibit 3).

Ascher, D.P., et al. (1992) Acidification Modified p24 Antigen Capture Assay in HIV Seropositives, *J. Acquired Imm. Def. Syn.* 5:1080–1083 (Exhibit 4).

Bollinger, R.C., et al. (1992) Acid Dissociation Increases the Sensitivity of p24 Antigen Detection for the Evaluation of Antiviral Therapy and Disease Progression in Asymptomatic Human Immunodeficiency Virus–Infected Persons, *J. Infect. Dis.* 165:913–916 (Exhibit 5).

Cheingsong–Popov, R., et al. (1990) Relation Between Humoral Responses to HIV gag and env Proteins at Seroconversion and Clinical Outcome of HIV infection, *Brit. Med. J.* 302:23–26 (Exhibit 6).

Harry, D.J., et al. (1989) Antigen Detection for Human Immunodeficiency Virus, *Clin. Microbiol. Rev.* 2:241–249 (Exhibit 7).

Healey, D.S., et al. (1988) A Preliminary Evaluation of Five Antigen Detection Assays, *J. Virol. Methods* 20:115–125 (Exhibit 8).

Lillo, F.B., et al. (1993) Improved Detection of Serum HIV p24 Antigen After Acid Dissociation of Immune Complexes, *AIDS* 7:1331–1336 (Exhibit 9).

McHugh, T.M., et al. (1988) Relation of Circulating Levels of Human Immunodeficiency Virus (HIV) Antigen, Antibody to p24, and HIV–Containing Immune Complexes in HIV–Infected Patients, *J. Infect. Dis.* 158:1088–1091.

Miles, S.A., et al. (1993) Rapid Serologic Testing with Immune–Complex–Dissociated HIV p24 Antigen for Early Detection of HIV Infection in Neonates *N. Eng. J. Med.* 162:21–28 (Exhibit 11).

Nishanian, P., et al. (1990) A Simple Method for Improved Assay Demonstrates That HIV p24 Antigen is Present as Immune Complexes in Most Sera from HIV–Infected Individuals, *J. Infect. Dis.* 162:21–28 (Exhibit 12).

Povolotsky, J., et al. (1992) Acid Treatment of Sera from HIV–1–Infected Children Substatially Increases the Sensitivity of the HIV p24 Antigen Immunoassay, *Pediatrics AIDS and HIV Infect.* 3:108–111 (Exhibit 13).

Quinn, T.C., et al. (1993) Acid Dissociation of Immune Complexes Improves Diagnostic Utility of p24 Antigen Detection in Perinatally Acquired Human Immunodeficiency Virus Infection, *J. Infect. Dis.* 167:1193–1196 (Exhibit 14).

Sei, Y. et al. (1989) Inverse Relationship Between HIV–1 p24 Antigenemia, Anti–p24 Antibody and Neutralizing Antibody Response in All Stages of HIV–1 Infection, *Imm. Letters* 20:233–230 (Exhibit 15).

Vasudevachari, M.B., et al. (1993) Clinical Utility of an Enhanced Human Immunodeficiency Virus Type 1 p24 Antigen Capture Assay, *J. Clin. Immunol.* 13:185–192 (Exhibit 16).

*Primary Examiner*—Christine M. Nucker
*Assistant Examiner*—Jeffrey Stucker
*Attorney, Agent, or Firm*—John P. White

[57] ABSTRACT

The present invention provides a method for determining the amount of HIV-1 p24 antigen or anti-HIV-1 p24 antibody present in a suitable bodily fluid sample from an HIV-1-infected subject. This invention also provides a kit for determining the amount of HIV-1 p24 antigen or anti-HIV-1 p24 antibody present in an HIV-1-infected subject.

8 Claims, No Drawings

METHOD FOR MEASURING ANTI-HIV-1 P24 ANTIBODY AND USE THEREOF

Throughout this application, various publications are referenced by Arabic numerals in brackets. Full citations for these publications may be found at the end of the specification immediately preceding the claims. The disclosures of these publications are in their entirety hereby incorporated by reference into this application to more fully describe the state of the art to which this invention pertains.

BACKGROUND OF THIS INVENTION

HIV-1 p24 antigen and anti-HIV-1 p24 antibody are important markers of HIV-1 reproduction and immune response. [1, 2, 5, 6, 8, 9, 13, 16, 18, 20–22, 25–28]. An intimate relationship exists between the presence of HIV-1 p24 antigen and the level of anti-HIV-1 p24 antibody in sera of HIV-1-infected subjects. A decrease in the level of anti-HIV-1 p24 antibody usually coincides with the appearance and persistence of circulating HIV-1 p24 antigen. Therefore, both of these markers are of great value for evaluating HIV-1 infection and predicting the progression in HIV-1-infected subjects.

HIV-1 p24 antigen and anti-HIV-1 p24 antibody detection assays are available as enzyme-linked immunosorbant assay (ELISA) kits from many commercial sources [10]. The detection of HIV-1 p24 antigen and anti-HIV-1 p24 antibody by existing kits are carried out separately, either in separate kits (e.g., Abbott) or in separate wells (e.g., Dupont HIV-1 p24 Core Profile ELISA, and Coulter HIV-1 p24 Antigen Assay System). The problem with the detection of HIV-1 p24 antigen and anti-HIV-1 p24 antibody separately is that in sera of HIV-1-infected subjects HIV-1 p24 antigen and anti-HIV-1 p24 antibody are usually present simultaneously and their interaction plays a crucial role in permitting their determination.

The basis of the above assay systems [10, 12, 14] is that immobilized anti-HIV-1 p24 antibody captures HIV-1 p24 antigen (in the DuPont, Coulter, Organon kits) or immobilized HIV-1 p24 antigen captures anti-HIV-1 p24 antibody (in the Abbott kits). In some kits (e.g., DuPont, Coulter), anti-HIV-1 p24 antibody is detected in a competition assay by using a mixture of a subject's serum with HIV-1 p24 antigen in wells with immobilized anti-HIV-1 p24 antibody.

SUMMARY OF INVENTION

The present invention provides a method for determining the amount of HIV-1 p24 antigen or anti-HIV-1 p24 antibody present in a suitable bodily fluid sample from an HIV-1-infected subject which comprises: (a) obtaining a suitable bodily fluid sample from the subject; (b) contacting the fluid sample with a suitable amount of immobilized anti-HIV-1 p24 antibody having already bound thereto a suitable amount of HIV-1 p24 antigen under conditions permitting the formation of a complex (i) between the HIV-1 p24 antigen present in the fluid sample and the immobilized anti-HIV-1 p24 antibody and (ii) between the anti-HIV-1 p24 antibody in the fluid sample and the immobilized HIV-1 p24 antigen, with the proviso that the immobilized anti-HIV-1 p24 antibody possesses a suitable number of vacant HIV-1 p24 antigen-binding sites prior to contacting with the fluid sample; (c) determining the total amount of HIV-1 p24 antigen present in the resulting complex; and (d) (1) comparing (i) the total amount of HIV-1 p24 antigen present in the resulting complex so determined to (ii) the total amount of HIV-1 p24 antigen bound to the immobilized anti-HIV-1 p24 antibody present prior to contacting with the fluid sample, the difference between (i) and (ii) being correlative with the amount of HIV-1 p24 antigen present in the fluid sample if (i) is greater than (ii), and correlative with the amount of anti-HIV-1 p24 antibody present in the fluid sample if (i) is less than (ii), comparing the difference between (i) and (ii) with a known standard so as to thereby determine the amount of HIV-1 p24 antigen or anti-HIV-1 p24 antibody present in the fluid sample.

In addition, this invention provides a method of determining the progression of an HIV-1 infection in a subject which comprises: (a) obtaining a first suitable bodily fluid sample from the subject and determining the amount of the HIV-1 p24 antigen or anti-HIV-1 p24 antibody present therein according to the method of claim 1; (b) after a suitable period of time obtaining a second suitable bodily fluid sample from the subject and determining the amount of HIV-1 p24 antigen or anti-HIV-1 p24 antibody present therein according to the method of claim 1; and (c) determining the difference between the amounts of HIV-1 antigen or anti-HIV-1 p24 antibody determined in steps (a) and (b), this difference being correlative with the progression of the HIV-1 infection in the subject, and comparing this difference with a known standard so as to thereby determine the progression of the HIV-1 infection in the subject.

In addition, this invention provides a method of determining the efficacy of a drug used to treat a subject infected with HIV-1 which comprises: (a) obtaining a suitable bodily fluid sample from a subject infected with HIV-1 and to whom the drug has been administered at a suitable point in time after commencement of the administering, and determining the amount of HIV-1 p24 antigen or anti-HIV-1 p24 antibody present therein according to the method of claim 1; and (b) comparing the amount of HIV-1 p24 antigen or anti-HIV-1 p24 antibody as so determined to a known standard so as to thereby determine the efficacy of the drug.

In addition, this invention provides a kit for determining the amount of HIV-1 p24 antigen or anti-HIV-1 p24 antibody present in a suitable bodily fluid sample from an HIV-1-infected subject which comprises: (a) a suitable amount of immobilized anti-HIV-1 p24 antibody having already bound thereto a suitable amount of HIV-1 p24 antigen, with the proviso that the immobilized anti-HIV-1 p24 antibody possesses a suitable number of vacant HIV-1 p24 antigen binding sites; and (b) an antibody capable of permitting the determination of HIV-1 p24 antigen.

Finally, this invention provides a kit for determining the amount of HIV-1 p24 antigen or anti-HIV-1 p24 antibody present in a suitable bodily fluid sample from an HIV-1-infected subject which comprises: (a) an anti-HIV-1 p24 antibody immobilized on a solid support; (b) a predetermined amount of HIV-1 p24 antigen; (c) an antibody capable of permitting the determination of HIV-1 p24 antigen; and (d) directions for use of the kit according to the method hereinabove described.

DETAILED DESCRIPTION OF THE INVENTION

The present invention provides a method for determining the amount of an HIV-related antigen or antibody specific therefor present in a fluid sample from an HIV-infected subject which comprises: (a) obtaining a suitable bodily fluid sample from the subject; (b) contacting the fluid sample with a suitable amount of immobilized antibody specific for the antigen, said antibody having already bound thereto a suitable amount of HIV-related antigen under conditions permitting the formation of a complex (i) between the HIV-related antigen present in the fluid sample and the immobilized antibody and (ii) between the antigen-specific antibody in the fluid sample and the immobilized antigen, with the proviso that the immobilized antibody possesses a suitable number of vacant HIV-related antigen-binding sites prior to contacting with the fluid sample; (c) determining the total amount of HIV-related antigen present in the resulting complex; and (d) (1) comparing (i) the total amount of HIV-related antigen present in the resulting complex so determined to (ii) the total amount of HIV-related antigen bound to the immobilized antibody prior to contacting with the fluid sample, the difference between (i) and (ii) being correlative with the amount of HIV-related antigen present in the fluid sample if (i) is greater than (ii), and correlative with the amount antigen-specific antibody present in the fluid sample if (i) is less than (ii), and (2) comparing the difference between (i) and (ii) with a known standard so as to thereby determine the amount of HIV-related antigen or antibody specific therefor present in the fluid sample.

As used herein, an "HIV-related antigen" includes, but is not limited to, the core protein gag gene product (i.e., p15, p17 and p18), envelope gene products (i.e., gp41, gp120 and gp160), pol gene products (i.e. p31), reverse transcriptase (i.e., gp66 and p151), and accessory gene products of HIV.

The present invention also provides a method for determining the amount of HIV-1 p24 antigen or anti-HIV-1 p24 antibody present in a suitable bodily fluid sample from an HIV-1-infected subject which comprises: (a) obtaining a suitable bodily fluid sample from the subject; (b) contacting the fluid sample with a suitable amount of immobilized antioHIV-1 p24 antibody having already bound thereto a suitable amount of HIV-1 p24 antigen under conditions permitting the formation of a complex (i) between the HIV-1 p24 antigen present in the fluid sample and the immobilized anti-HIV-1 p24 antibody and (ii) between the anti-HIV-1 p24 antibody in the fluid sample and the immobilized HIV-1 p24 antigen, with the proviso that the immobilized anti-HIV-1 p24 antibody possesses a suitable number of vacant HIV-1 p24 antigen-binding sites prior to contacting with the fluid sample; (c) determining the total amount of HIV-1 p24 antigen present in the resulting complex; and (d) (1) comparing (i) the total amount of HIV-1 p24 antigen present in the resulting complex so determined to (ii) the total amount of HIV-1 p24 antigen bound to the immobilized anti-HIV-1 p24 antibody prior to contacting with the fluid sample, the difference between (i) and (ii) being correlative with the amount of HIV-1 p24 antigen present in the fluid sample if (i) is greater than (ii), and correlative with the amount anti-HIV-1 p24 antibody present in the fluid sample if (i) is less than (ii), and (2) comparing the difference between (i) and (ii) with a known standard so as to thereby determine the amount of HIV-1 p24 antigen or anti-HIV-1 p24 antibody present in the fluid sample.

The quantitative determination of anti-HIV-1 p24 antibody is important in the evaluation of the progression or activity of HIV-1 infection. The anti-HIV-1 p24 antibody includes, but is not limited to, IgG, IgM, IgA, IgE, or IgD.

The suitable bodily fluid sample is any bodily fluid sample which would contain either HIV-1 p24 antigen or anti-HIV-1 p24 antibody in an HIV-1-infected subject. A suitable bodily fluid includes, but is not limited to, serum, plasma, cerebrospinal fluid, sperm, sputum and urine. In the preferred embodiment, the suitable bodily fluid sample is serum or plasma. In addition, the body fluid sample may be a superhate from a cell culture. Methods of obtaining a suitable bodily fluid sample from a subject are known to those skilled in the art.

The "amount" of HIV-1 p24 antigen or anti-HIV-1 p24 antibody determined by the method of the subject invention may be an actual amount, e.g. expressed as a concentration of pg/ml, or a number which correlates with the actual amount thereof in a fluid sample.

As used herein, "an HIV-1-infected subject" means a subject who is infected with HIV-1, i.e. a subject having $CD4^+$ cells which have been invaded by HIV-1. The subject may be a human, monkey, dog, cat, rabbit or rodent (e.g. mouse). In the preferred embodiment the subject is a human.

The contacting of the fluid sample with an immobilized anti-HIV-1 p24 antibody may be carried out under conditions well known to those skilled in the art. Such conditions are exemplified, but not limited to, those in the Experimental Details section which follows.

The "suitable amount of immobilized anti-HIV-1 p24 antibody" is the amount of anti-EIV-1 p24 antibody immobilized upon contacting a plastic well with 1–100 µg/ml of anti-HIV-1 p24 antibody for a suitable period of time. In another embodiment the suitable amount of immobilized anti-HIV-1 p24 antibody is the amount immobilized upon contact with 20–50 µg/ml of anti-HIV-1 p24 antibody for a suitable period of time. In the preferred embodiment the suitable amount of immobilized anti-HIV-1 p24 antibody is the amount immobilized upon contact with 30 µg/ml of anti-HIV-1 p24 antibody for a suitable period of time. Suitable amounts of immobilized anti-HIV-1 p24 antibody are exemplified by, but not limited to, those in the Experimental Details section which follows.

The anti-HIV-1 p24 antibody may be immobilized on any suitable solid matrix known in the art. In the preferred embodiment, the anti-HIV-1 p24 antibody is immobilized on the surface of a plastic assay well. Methods of immobilizing antibodies are well known to those skilled in the art.

The "suitable amount of HIV-1 p24 antigen" bound to immobilized anti-HIV-1 p24 antibody is an amount of HIV-1 p24 antigen such that when bound to the immobilized anti-HIV-1 p24 antibody, the immobilized anti-HIV-1 p24 antibody possesses a suitable number of vacant HIV-1 p24 antigen-binding sites prior to contact with the sample. A suitable number of vacant HIV-1 p24 antigen-binding sites is defined as enough antigen binding sites to accommodate all HIV-1 p24 antigen present in the sample contacted with the immobilized anti-HIV-1 p24 antibody. The suitable amount of HIV-1 p24 antigen may be calculated in a manner known to those skilled in the art.

In one embodiment, the suitable amount of HIV-1 p24 antigen is the amount of HIV-1 p24 antigen complexed with the immobilized anti-HIV-1 p24 antibody upon contacting therewith 10–3000 pg/ml of HIV-1 p24 antigen for a suitable period of time. Alternatively, this antigen concentration range may be 10–100 pg/ml, 10–50 pg/ml, and preferably 30–50 pg/ml. Suitable amounts of HIV-1 p24 antigen are exemplified by, but not limited to, those in the Experimental Details section which follows.

The conditions permitting complex formation between the HIV-1 p24 antigen of the fluid sample and the immobilized anti-HIV-1 p24 antibody, and between the immobilized HIV-1 p24 antigen and the anti-HIV-1 p24 antibody of the fluid sample, are known to those skilled in the art.

The method of this invention permits the determination of the amount of HIV-1 p24 antigen or anti-HIV-1 p24 antibody present in a fluid sample based on contacting the fluid sample with a stable complex between HIV-1 p24 antigen and immobilized anti-HIV-1 p24 antibody.

In one embodiment, the immobilized HIV-1 p24 antigen/ anti-HIV-1 p24 antibody complex is prepared immediately prior to contacting with the fluid sample. In the preferred embodiment, the complex is prepared no more than 2–3 hours prior to contacting with the fluid sample.

For example, if a fluid sample comprises a greater amount of HIV-1 p24 antigen than anti-HIV-1 p24 antibody, the total amount of HIV-1 p24 antigen immobilized in the well will increase after contacting with the sample in proportion to the amount of HIV-1 p24 antigen present in the fluid sample. However, if a fluid sample comprises a greater amount of anti-HIV-1 p24 antibody than HIV-1 p24 antigen, the total amount .of detectable HIV-1 p24 antigen in the well will decrease after contacting with the sample in proportion to the amount of anti-HIV-1 antibody present in the sample. In an HIV-1-infected subject's bodily fluid, only two scenarios can occur: (a) there is a greater amount of HIV-1 p24 antigen than anti-HIV-1 p24 antibody; or (b) there is a greater amount of anti-HIV-1 p24 antibody than HIV-1 p24 antigen.

Quantitatively determining HIV-1 p24 antigen may be accomplished by well known methods. For example, one may employ ELISA, RIA, or colorimetric enzymes techniques, which are known to those skilled in the art.

As used herein, "known standard" includes but is not limited to, controls for (a) antigen, (e.g. HIV-1-negative serum spiked with HIV-1 p24 antigen, for example at a concentration of 25 pg/ml), and (b) antibody, (e.g. anti-HIV-1 p24 antibody which can bind to 100% of the immobilized HIV-1 p24 antigen in the HIV-1 p24 antigen/anti-HIV-1 p24 antibody complex. However, other standards which are known to those skilled in the art may be employed.

In one embodiment, the fluid sample may be additionally treated with a suitable acid or base. The suitable acid includes, but is not limited to, hydrochloric acid and glycine hydrochloride. The suitable base includes, but is not limited to, sodium hydroxide. Methods of treating with acid or base are exemplified in the Experimental Details section below.

The treatment of a fluid sample with acid or base destroys anti-HIV-1 p24 antibody present therein. This further facilitates the quantitative determination of anti-HIV-1 p24 antibody present in the sample. If the amount of anti-HIV-1 p24 antibody is high in acid or base-treated serum, i.e. more than 70% of the index of neutralization, the level of HIV-1 p24 antigen is thereafter determined in untreated serum diluted to 1:10, 1:100, 1:1000, and 1:10,000.

In addition, this invention provides a method of determining the progression of an HIV-1 infection in a subject which comprises: (a) obtaining a first suitable bodily fluid sample from the subject and determining the amount of the HIV-1 p24 antigen or anti-HIV-1 p24 antibody present therein according to the method of the subject invention; (b) after a suitable period of time obtaining a second suitable bodily fluid sample from the subject and determining the amount of HIV-1 p24 antigen or anti-HIV-1 p24 antibody present therein according to the method of the subject invention; and (c) determining the difference between the amounts of HIV-1 antigen or anti-HIV-1 p24 antibody determined in steps (a) and (b), this difference being correlative with the progression of the HIV-1 infection in the subject, and comparing this difference with a known standard so as to thereby determine the progression of the HIV-1 infection in the subject.

As used herein, "the progression of HIV-1-infection" means the increase in activity of the HIV-1 infection in a subject, which activity is correlative with the amount of HIV-1 p24 antigen present in the subject, and inversely correlative with the amount of anti-HIV-1 p24 antibody present in the subject infected with HIV-1.

For example, if the amount of anti-HIV-1 p24 antibody is decreasing, or if the amount of HIV-1 p24 antigen is increasing, the activity of the HIV-1 infection is increasing. Alternatively, if the amount of HIV-1 p24 antigen is decreasing or the amount of HIV-1 p24 antibody is increasing, the activity of the HIV-1 infection is decreasing. Knowledge of the activity of HIV-1-infection is useful in determining the efficacy of anti-HIV therapy.

As used herein a "suitable period of time" for determining the progression of an HIV-1-infection may be determined by methods known to those skilled in the art. In one embodiment, the suitable period of time is 6 months. In another embodiment, the suitable period of time is a year or more.

In addition, this invention provides a method of determining the efficacy of a drug used to treat a subject infected with HIV-1 which comprises: (a) obtaining a suitable bodily fluid sample from a subject infected with HIV-1 and to whom the drug has been administered, at a suitable point in time after commencement of the administering, and determining the amount of HIV-1 p24 antigen or anti-HIV-1 p24 antibody present therein according to the method of the subject invention; and (b) comparing the amount of HIV-1 p24 antigen or anti-HIV-1 p24 antibody so determined to a known standard so as to thereby determine the efficacy of the drug.

The drug may be any type of drug used to treat a subject infected with HIV-1. More specifically, the drug may be, for example, an antiviral drug, e.g. AZT. Further, the suitable time for obtaining the bodily fluid sample after administration of the drug may be determined according to methods known to those skilled in the art.

In one embodiment the suitable bodily fluid sample is obtained during administration of the drug. In a second embodiment, the suitable bodily fluid sample is obtained after cessation of administration of the drug. In a third embodiment, the suitable bodily fluid sample is obtained at multiple points during drug administration.

In one embodiment, the known standard is obtained using a sample taken from the subject prior to administration of the drug. In another embodiment, the known standard is obtained using the sample taken from another subject prior to administration of the drug.

In addition, this invention provides a kit for determining the amount of HIV-1 p24 antigen or anti-HIV-1 p24 antibody present in a suitable bodily fluid sample from an HIV-1-infected subject which comprises: (a) a suitable amount of immobilized anti-HIV-1 p24 antibody having already bound thereto a suitable amount of HIV-1 p24 antigen, with the proviso that the immobilized anti-HIV-1 p24 antibody possesses a suitable number of vacant HIV-1 p24 antigen binding sites; and (b) an antibody capable of permitting the quantitative determination of HIV-1 p24 antigen.

The detectable antibody may be labeled with an enzyme, fluorescent, or radiolabel marker. The kit may further comprise a second antibody labeled with an enzyme, fluorescent, or radiolabel marker. Methods of labelling are well known to those in the art.

Finally, this invention provides a kit for determining the amount of HIV-1 p24 antigen or anti-HIV-1 p24 antibody present in a suitable bodily fluid sample from an HIV-1-infected subject which comprises: (a) a suitable amount of immobilized anti-HIV-1 p24 antibody; (b) a predetermined amount of HIV-1 p24 antigen; (c) an antibody capable of permitting the determination of HIV-1 p24 antigen; and (d) directions for use of the kit according to the method hereinabove described.

This invention is further illustrated in the Experimental Details section which follows. This section is set forth to aid in an understanding of the invention but is not intended to, and should not be construed to, limit in any way the invention as set forth in the claims which follow thereafter.

EXPERIMENTAL DETAILS

Materials and Methods

Subjects: Homosexual, and heterosexual men and women, and children, testing positive for HIV, participating in the AIDS Clinical Trials Group (ACTG) New York, were studied. These individuals have been followed at 6-month intervals and 1 year intervals between 1988 and 1993. Serum samples were obtained from the peripheral blood of 107 seropositive HIV-1 subjects randomly selected. Blood samples were collected and the serum separated under aseptic conditions, stored at −70° C. and thawed on the day of the experiments. Sera were tested for the presence of antibodies using a commercial ELISA test and confirmed by Western blot analysis.

Example 1: Determination of HIV-1 p24 Antigen or anti-HIV-1 p24 Antibody

For determination of HIV-1 p24 antibody or HIV-1 p24 antigen simultaneously, serum (plasma) samples were treated with acid (pH 1.2–1.5) [for the effect of acid treatment, see 3, 4, 15, 17, 19, 23, 24] and HIV-1 p24 antigen bound to immobilized anti-HIV-1 p24 antibody was used to capture HIV-1 p24 antigen and anti-HIV-1 p24 antibody.

Commercially available HIV-1 p24 antigen ELISA kits manufactured by Coulter and DuPont (Dupont HIV-1 p24 Core Profile ELISA, and Coulter HIV-1 p24 Antigen Assay System) were used to determine the amount of HIV-1 p24 antigen and anti-HIV-1 p24 antibody in subjects' sera by HIV-1 p24 antigen/anti-HIV-1 p24 antibody complex. In these kits mouse anti-HIV-1 p24 monoclonal antibody was bound to the microplate wells as the captured antibody. HIV-1 p24 antigen (as provided by the kits) in an amount of 30–50 pg/ml was added to microplate wells for one hour at 37° C., and after washing 3 times by washing buffer, an immobilized anti-HIV-1 p24 antibody/HIV-1 p24 antigen immune complex was made.

For acid treatment, 100 μL of serum (plasma) sample were mixed with 100 μL of 0.33 N HCl (pH 1.2–1.5) and the mixture incubated for one hour at 37° C. 100 μL of 0.33 N NaOH were then added for acid neutralization (pH 6.5–7.0). 200 μl of the neutral mixture were used for determination of HIV-1 p24 antigen and anti-HIV-1 p24 antibody in wells with immobilized anti-HIV-1 p24 antibody/HIV-1 p24 antigen immune complex in commercially available HIV-1 p24 antigen ELISA kits according to the manufacturers' instructions. For base treatment, 100 μL of serum were treated with 25 μL of base in a well with immobilized HIV-1 p24 antigen/anti-HIV-1 p24 antibody in an HIV-1 p24 ELISA kit (Organon) for 18 hours at room temperature.

Acid or base treatment considerably facilitated the determination of HIV-1 p24 antigen. The data demonstrate that if in untreated serum anti-HIV-1 p24 antibody titers are high, antibody may remain detectable following acid or base treatment. Table 1 demonstrates a decrease in the amount of anti-HIV-1 p24 antibody in sera of asymptomatic HIV-1-infected subjects from 1988 to 1993. Dilutions of the untreated serum were 1:10, 1:100, 1:1000 and 1:10,000 with an immune complex absorbance of 0.707. Table 2 demonstrates determination of HIV-1 p24 antigen and anti-HIV-1 p24 antibody in wells with immune complex with base treated serum with an immune complex absorbance of 0.917. Table 3 demonstrates absorbance of serum treated with acid of HIV-1-infected subjects with an immune complex absorbance of 0.670. Table 4 demonstrates the absorbance of untreated serum and acid treated serum of women infected with HIV-1. Dilutions of the untreated serum were 1:10, 1:100, and 1:1000 with an immune complex absorbance of 0.617. Table 5 demonstrates absorbance of untreated serum and acid treated serum of children infected with HIV-1 with an immune complex absorbance of 0.349.

Example 2: Kit for determining HIV-1 p24 Antigen or anti-HIV-1 p24 Antibody

Reagents used for the kits include: antibody coated microfilter plate, uncoated strip, plate covers, stop solution, lyse buffer, antigen reagent (lyophilized), CH-biotin reagent (lyophilized), normal human serum (NHS), SA-HRPO, SA-buffer (21.0 mL), TMB reagent (0.5 mL), TMB diluent (21.0 mL), wash Buffer (20×Conc) (75.0 mL), CBR-1 (5.0 mL). Human serum nonreactive for HIV-1 antibody. The base dissociation reagent may contain: 0.1% gentamicin and 0.02% cinnamaldehyde as preservatives and D%C green dye no. 5 as coloring agent.

By way of example, the kit may include one or more of the following: immobilized anti-HIV-1 p24 antibody/HIV-1 p24 antigen complex; Tris buffer containing detergent and 0.02% Sodium Azide as a preservative; phosphate buffered saline (PBS) containing added protein, detergent, and 0.1% sodium azide as preservative; disruption buffer which is added to disrupt any HIV-1 virions present in test specimens; streptavidin-HRP diluent—14 mL PBS containing added protein, strip(s) OPD tablets—5 tablets per strip, 60 mL citrate buffer containing 2-chloroacetamide and 0.03 % hydrogen peroxide; and horseradish peroxidase labeled anti-HIV-1 (human) (containing 0.01% gentamicin and 0.2% cinnamaldehyde as preservatives).

Discussion

The method of determining HIV-1 p24 antigen and anti-HIV-1 p24 antibody may employ the following controls: (1) control of HIV-1 p24 antigen in immobilized immune complex (the average of absorbances of the 3 wells with HIV-1 negative serum); (2) HIV-1 p24 antigen positive control (HIV-1-negative serum spiked with HIV-1 p24 antigen—1 well); (3) HIV-1 p24 antibody-positive control (HIV-1-negative serum spiked with HIV-1 p24 antibody which can neutralize 100% of HIV-1 p24 antigen in immobilized immune complex—3 wells); and (4) Immune complex positive control (HIV-1-negative sera with HIV-1 p24 antigen/ anti-HIV-1 p24 antibody immune complex in sera which becomes positive for HIV-1 p24 antigen after treatment with acid or base—1 well).

The presence of anti-HIV-1 p24 antibody is determined by the index of antigen neutralization. If the mean absorbance of HIV-1 p24 antigen of an HIV-1-infected subject decreases as compared to the known standard, the subject is considered to be positive for the presence of anti-HIV-1 p24 antibody.

Index of Antigen Neutralization =

$$\frac{(\text{Antigen mean absorbance} - \text{Sample Absorbance})}{\text{Antigen mean absorbance}} \times 100$$

The presence of HIV-1 p24 antigen is determined by the index of antigen determination. If the mean absorbance of HIV-1 p24 antigen from a serum sample of an HIV-1-infected subject increases as compared to the known standard, the subject is considered to be positive for the presence of HIV-1 p24 antigen.

Index of Antigen Determination =

$$\frac{(\text{Sample absorbance} - \text{Antigen mean absorbance})}{\text{Antigen mean absorbance}}$$

For example, if the well contains a concentration of 40 pg/ml of HIV-1 p24 antigen (which maintains an absorbance of 1000 nm) and thereafter increases to 1500 nm when serum is added, the index of antigen determination would be 0.5, which means that 20 pg/ml of HIV-1 p24 antigen is in the serum sample.

When the absorbance of HIV-1 p24 antigen decreases, or is less than the known standard, then the amount of anti-HIV-1 p24 antibodies in a serum sample is said to increase and can be so determined. For example, if the well contains a concentration of 40 pg/ml of HIV-1 p24 antigen (which maintains an absorbance of 1000 nm) and thereafter decreases to 500 nm when serum is added, the index of neutralization would be 50%. The highest dilution that neutralizes HIV-1 p24 antigen in HIV-1 p24 antigen/anti-HIV-1 p24 antibody immune complex is considered as a titre of the anti HIV-1 p24 antibody.

Determination of HIV-1 p24 antigen and anti-HIV-1 p24 antibody by the immobilized anti-HIV-1 p24 antibody/HIV-1 p24 antigen complex is demonstrated in Table 6.

TABLE 1

| Patients | | 1:10 | | 1:100 | | 1:1,000 | | 1:10,000 | | Titer |
|---|---|---|---|---|---|---|---|---|---|---|
| 1 | 1988 | 0.97 | (86.3%) | .113 | (84.0%) | .263 | (62.8%) | .557 | (21.2%) | 1:100 |
|   | 1993 | .100 | (85.9%) | .161 | (71.2%) | .467 | (34.0%) | .694 | (1.8%) | 1:10 |
| 2 | 1988 | 0.90 | (87.3%) | .113 | (84.0%) | .331 | (53.2%) | .612 | (13.4%) | 1:100 |
|   | 1993 | .119 | (83.2%) | .154 | (78.2%) | .451 | (36.2%) | .645 | (8.2%) | 1:10 |
| 3 | 1988 | 0.99 | (86.0%) | .131 | (81.5%) | .425 | (39.9%) | .683 | (3.4%) | 1:100 |
|   | 1993 | .135 | (80.9%) | .375 | (47.0%) | .692 | (2.1%) | .678 | (4.1%) | 1:10 |
| 4 | 1988 | 0.97 | (86.3%) | .130 | (81.5%) | .447 | (36.8%) | .647 | (8.5%) | 1:100 |
|   | 1993 | .109 | (84.6%) | .299 | (58.7%) | .525 | (25.4%) | .603 | (14.7%) | 1:10 |

TABLE 2

| Patients with AIDS | Absorbance of base treated serum | |
|---|---|---|
| 1 | .521 | |
| 2 | .130 | (85.8%) |
| 3 | .861 | |
| 4 | .383 | |
| 5 | .967 | |
| 6 | 1.104 | |
| 7 | 1.958 | |
| 8 | 3.337 | |
| 9 | 2.211 | |
| 10 | 2.590 | |
| 11 | .476 | |
| 12 | .154 | (83.2%) |
| 13 | 0.98 | (89.3%) |
| 14 | .667 | |
| 15 | .241 | |
| 16 | .400 | |
| 17 | .738 | |
| 18 | .583 | |
| 19 | .446 | |
| 20 | .583 | |
| 21 | 0.83 | (90.9%) |

TABLE 3

| Patient No. | 1988 Year | | Year |
|---|---|---|---|
| 1 | .148 | .242 | 1993 |
| 2 | .195 | .354 | 1993 |
| 3 | .581 | 1.992 | 1993 |
| 4 | .288 | .410 | (1991 year) |
| 5 | .418 | .579 | (1991 year) |
| 6 | .212 | .509 | 3.993 |
| 7 | .476 | .500 | (1992 year) |
| 8 | .450 | .570 | 1993 |
| 9 | .126 | .410 | (1991 year) |
| 10 | 1.161 | 1.692 | 1993 |
| 11 | .510 | .695 | 1993 |
| 12 | .181 | .731 | 1993 |

TABLE 4

| | Dilutions of untreated serum | | | | |
|---|---|---|---|---|---|
| Women Infected With HIV-1 | Untreated Serum | Acid Treated Serum | 1:10 | 1:100 | 1:1000 |
| 1 | .044 | .593 | .545 | .562 | .631 |
| 2 | .061 | .584 | .387 | .424 | .448 |
| 3 | .025 | .091 | .176 | .191 | .428 |
| 4 | .025 | .076 | .157 | .190 | .210 |

TABLE 4-continued

| | Dilutions of untreated serum | | | | |
|---|---|---|---|---|---|
| Women Infected With HIV-1 | Untreated Serum | Acid Treated Serum | 1:10 | 1:100 | 1:1000 |
| 5 | .017 | .044 | .078 | .089 | .129 |
| 6 | .029 | .037 | .080 | .095 | .124 |
| 7 | .028 | .090 | .59 | .095 | .180 |
| 8 | .064 | 1.702 | .423 | .561 | .666 |
| 9 | .020 | .171 | .074 | .166 | .303 |
| 10 | .071 | 1.084 | .412 | .371 | .444 |
| 11 | 0.025 | .214 | .120 | .214 | .439 |
| 12 | 0.039 | .459 | .264 | .414 | .482 |

TABLE 5

| N Serum | Untreated | (Acid Treated) × (3 − dilution factor) |
|---|---|---|
| 1 | .508 | 3.904 = 11.712 |
| 2 | .600 | .946 = 2.838 |
| 3 | .805 | 2.816 = 8.448 |
| 4 | 1.251 | .854 = 2.562 |
| 5 | .714 | .597 = 1.791 |
| 6 | .456 | .777 = 2.331 |
| 7 | .132 | .379 = 1.137 |
| 8 | .430 | .762 = 2.286 |
| 9 | 1.043 | 1.420 = 4.26 |
| 10 | 1.071 | 3.992 = 11.976 |

TABLE 6

| N/N | Determination of anti-HIV-1 p24 antibody or HIV-1 p24 antigen in acid treated serum | Number of patients | |
|---|---|---|---|
| | Index of antigen neutralization (anti-HIV-1 p24 antibody determination) | | |
| 1 | >70% | 9 | 8.4% |
| 2 | 51%–70% | 21 | 19.6% |
| 3 | 25%–50% | 14 | 13.1% |
| 4 | <25% | 19 | 17.8% |
| | Index of antigen determination (HIV-1 p24 antigen determination) | | |
| 5 | <.025 | 6 | 5.6% |
| 6 | .025–0.50 | 14 | 13.1% |
| 7 | >.050–1.0 | 7 | 6.5% |
| 8 | >1.0 | 17 | 15.9% |

REFERENCES

1. Allain, J. P., et al. (1986) *Lancet* 2:1233–6.
2. Andrieu, J. M., et al. (1988) *Clinical Experimental Immunology* 73:1–51.
3. Ascher, D. P., et al. (1992) *The Journal of Acquired Immune Deficiency Syndrome* 5:1080–1085.
4. Bollinger, R. C., et al. (1992) *The Journal of Infectious Diseases* 165:913–916.
5. Chargelegue, D., et al. (1993) *The Journal of Acquired Immune Deficiency Syndrome* 7:S87–S90.
6. Cheingsong-Popov, R., et al. (1991) *British Medical Journal* 302:23–26.
7. Dawson, G. J., et al. (1986) Programs and abstracts of the II International Conference on AIDS, Paris, Facimprim, Abstract No. 642.
8. Fenouillet, E., et al. (1992) *The Journal of Infectious Diseases* 166:611–616.
9. Goudsmit J, et al. (1986) *Lancet* 2:177–80.
10. Harry, D. J., et al. (1989) *Clinical Microbiology Reviews* 241–249.
11. Healy, D. S., et al. (1988) *J. Virol Methods* 20:115–125.
12. Hevey, et al. U.S. Pat. No. 4,228,237, issued Oct. 14, 1980.
13. Janvier, B., et al. (1993) *The Journal of Acquired Immune Deficiency Syndrome* 6:898–903.
14. Kortright, et al., U.S. Pat. No. 4,886,742, issued Dec. 12, 1989.
15. Lillo, F. B., et al. (1993) *The Journal of Acquired Immune Deficiency Syndrome* 7:1331–1336.
16. McRae, B., et al. (1991) *AIDS Research and Human Retroviruses* 7:637–643.
17. Miles, S. A. et al. (1993) *The New England Journal of Medicine* 328:297–302.
18. Morrow, W. J. W., et al. (1991) *Clin. Immunol. Immunopathol.* 58:163–180.
19. Nishanian, P., et al. (1990) *The Journal of Infectious Diseases* 162:21–28.
20. Nishanian, P., et al. (1987) *J. Clin. Microbiol.* 23:395–400.
21. Pedersen, C., et al. (1987) *British Medical Journal* 295:567–569.
22. Phillips, A. N., et al. (1991) *AIDS* 5:1217–1222.
23. Povolotsky, J., et al. (1992) *Pediatric AIDS and HIV Infection: Fetus to Adolescent* 3:108–111.
24. Quinn, T. C., et al. (1993) *The Journal of Infectious Diseases* 167:1193–1196.
25. Sei, Y., et al. (1989) *Immunology Letters* 20:223–230.
26. Spector, S. A., et al. (1989) *The Journal of Infectious Diseases* 159:822–828.
27. Vasudevachari, M. B., et al. (1993) *Journal of Clinical Immunology* 13:185–192.
28. Wolf, F., et al. (1988) *The Journal of Infectious Diseases* 158:615–622.

What is claimed is:

1. A method for measuring the amount of anti-HIV-1 p24 antibody obtained from a suitable bodily fluid sample from an HIV-1-infected subject which comprises:

(a) contacting a predetermined amount of immobilized anti-HIV-1 p24 antibody with a known nonsaturating amount of HIV-1 p24 antigen under conditions permitting binding of the HIV-1 p24 antigen to the immobilized anti-HIV-1 p24 antibody so as to form a first complex;

(b) removing any unbound HIV-1 p24 antigen;

(c) contacting the bodily fluid sample with the first complex under conditions permitting binding of anti-HIV-1 p24 antibody in the sample to the first complex so as to form a second complex;

(d) removing any unbound anti-HIV-1 p24 antibody;

(e) contacting the second complex with a labeled antibody which specifically binds to any HIV-1 p24 antigen not present in the second complex;

(f) removing any unbound labeled antibody; and (g) quantitatively determining the amount of labeled antibody bound to HIV-1 p24 antigen so as to thereby quantitatively determine the amount of anti-HIV-1 p24 antibody present in the second complex.

2. The method of claim 1, wherein the bodily fluid sample is selected from the group consisting of serum, plasma, cerebrospinal fluid, sperm, sputum and urine.

3. The method of claim 1, wherein before step (c) the bodily fluid sample is treated with acid.

4. The method of claim 1, wherein before step (c) the bodily fluid sample is treated with base.

5. The method of claim 1, wherein before step (c) the bodily fluid is serially diluted.

6. The method of claim 1, wherein the subject is a human.

7. A method for determining the progression of an HIV-1 infection in a subject which comprises:
   (a) obtaining at least two suitable bodily fluid samples from the subject at different times;
   (b) measuring the amount of anti-HIV-1 p24 antibody present in each such sample according to the method of claim 1; and
   (c) determining the difference between the amounts of anti-HIV-1 p24 antibody measured in such samples so as to thereby determine the progression of the HIV-1 infection in the subject.

8. A method for determining the efficacy of a drug for treating a subject infected with HIV-1 which comprises:
   (a) obtaining at least two suitable bodily fluid samples from the subject at different times after the drug has been administered to the subject; and
   (b) measuring the amount of anti-HIV-1 p24 antibody present in each such sample according to the method of claim 1 so as determine the efficacy of the drug.

* * * * *